United States Patent [19]

Ohashi et al.

[11] 4,319,040
[45] Mar. 9, 1982

[54] PROCESS FOR THE PRODUCTION OF OPTICALLY ACTIVE THREO-3-(3,4-DIHYDROXYPHENYL)SERINE

[75] Inventors: Naohito Ohashi, Nishinomiya; Shoji Nagata, Toyonaka; Kikuo Ioshizumi, Toyonaka; Junki Katsube, Toyonaka, all of Japan

[73] Assignee: Sumitomo Chemical Company, Limited, Osaka, Japan

[21] Appl. No.: 170,152

[22] Filed: Jul. 18, 1980

[30] Foreign Application Priority Data

Aug. 20, 1979 [JP] Japan ............................ 54-106483

[51] Int. Cl.$^3$ ............................................ C07B 19/00
[52] U.S. Cl. ................................... 562/401; 560/42; 562/444
[58] Field of Search ................... 562/401, 444; 560/42

[56] References Cited

U.S. PATENT DOCUMENTS 3,920,728  11/1975  Hegedus et al. ................. 562/401

FOREIGN PATENT DOCUMENTS 52-65242   5/1977   Japan .
785014    10/1957   United Kingdom .

*Primary Examiner*—Natalie Trousof
*Assistant Examiner*—Vera C. Clarke
*Attorney, Agent, or Firm*—Birch, Stewart, Kolasch & Birch

[57] ABSTRACT

Improved process for the production of optical aCTIVE (D- or L-) threo-3-(3,4-dihydroxyphenyl)serine, which comprises subjecting racemic threo-3-(3,4-dibenzyloxyphenyl)-N-carbobenzyloxyserine to optical resolution by using as a resolving reagent an optical active amino alcohol derivative, and then subjecting the resulting optical active (D- or L-) threo-3-(3,4-dibenzyloxyphenyl)-N-carbobenzyloxyserine to hydrogenolysis.

7 Claims, No Drawings

PROCESS FOR THE PRODUCTION OF OPTICALLY ACTIVE THREO-3-(3,4-DIHYDROXYPHENYL)SERINE

The present invention relates to a process for the production of optically active threo-3-(3,4-dihydroxyphenyl)serine (hereinafter referred to as "DOPS") which is useful as a medicine.

It is known that optically active (D- or L-) threo-DOPS is a precursor of norepinephrine which is an important catecholamine in the living body, and that this threo-DOPS has activities on the circulation system and psychotropic activities (c.f. Japanese Patent Publication (unexamined) No. 49252/1975).

There have been known various processes for the production of optically active (D- or L-) threo-DOPS as disclosed, for example, in Japanese Patent Publication (unexamined) Nos. 49252/1975, 32540/1976, and 36233/1979. However, according to the processes as disclosed in Japanese Patent Publication (unexamined) Nos. 49252/1975 and 36233/1979, a suitable resolving reagent for resolving the racemic mixture into the optically active isomers is hardly obtainable. Besides, according to the process as disclosed in Japanese Patent Publication (unexamined) No. 32540/1976, a racemic mixture of threo-DOPS is firstly prepared and then the racemic mixture is subjected to optical resolution, which is unfavorable from an economical viewpoint.

As a result of the present inventors' intensive study on an improved process for the production of optically active threo-DOPS, it has been found that an economical and industrial production of the desired optically active (D- or L-) threo-DOPS can be achieved by firstly subjecting a racemic protected DOPS to optical resolution with a specific resolving reagent and then subjecting the resulting optically active protected DOPS to hydrogenolysis.

An object of the present invention is to provide an improved process for the production of optically active (D- or L-) threo-DOPS. Other object and advantages of the present invention will be apparent to persons skilled in the art from the following description.

The improved process of the present invention comprises subjecting racemic threo-3-(3,4-dibenzyloxyphenyl)-N-carbobenzyloxyserine of the formula:

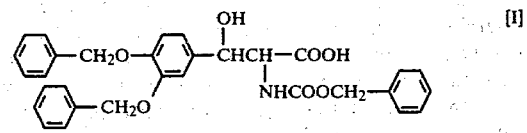

to optical resolution with an optical active amino alcohol derivative of the formula:

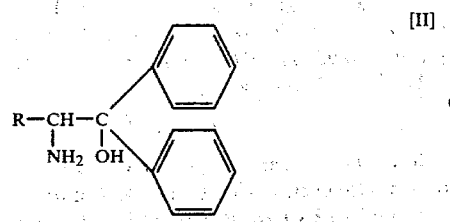

wherein R is methyl, isopropyl or isobutyl, and then subjecting the resulting optically active (D- or L-) threo-3-(3,4-dibenzyloxyphenyl)-N-carbobenzyloxyserine to hydrogenolysis to give the desired optically active (D- or L-) threo-DOPS.

According to the present invention, the diastereomer salts obtained by the reaction of the racemic 3-(3,4-dibenzyloxyphenyl)-N-carbobenzyloxyserine [I] with the otpically active amino alcohol derivative [II] have different solubility, and owing to the different solubility, the racemic mixture of diastereomer salts can be separated into each diastereomer salt, i.e. D-3-(3,4-dibenzyloxyphenyl)-N-carbobenzyloxyserine.amino alcohol derivative salt and L-3-(3,4-dibenzyloxyphenyl)-N-carbobenzyloxyserine.amino alcohol derivative salt. The diastereomer salts thus resolved are each decomposed with an acid to obtain optically active (D- or L-) 3-(3,4-dibennzyloxyphenyl)-N-carbobenzyloxyserine, which is then subjected to hydrogenolysis.

The process of the present invention is advantageous for the economical and industrial production of the desired optically active (D- or L-) threo-DOPS in view of the easy availability or the starting materials and high optical resolution yield.

The process of the present invention is disclosed in more detail below.

An equimolar or less amount of optically active (S- or R-) amino alcohol derivative [II] is added to racemic threo-3-(3,4-dibenzyloxyphenyl)-N-carbobenzyloxyserine [I] in a solvent to prepare a solution containing diastereomer salts. The amount of the resolving reagent may vary, but is usually in the range of 0.5 to 1 mole per 1 mole of the racemic mixture to be resolved. When the optically active resolving reagent is used in an amount of less than 1 mole (e.g. 0.5 mole), the remaining amount (e.g. 0.5 mole) of an optically inactive amine or an inorganic base may be added.

The solvent used in the present invention is a neutral solvent. Acidic solvents (e.g. acetic acid) and basic solvents (e.g. amines) are excluded because they inhibit the formation of the diastereomer salts. In view of the easy operability and low cost, suitable examples of the solvent are ketones such as acetone or methyl ethyl ketone, alcohols having 1 to 4 carbon atoms such as methanol, ethanol or isopropanol, or aqueous mixture of these ketones or alcohols, or ethyl acetate, toluene, acetonitrile, dichloroethane, or a mixture thereof. Preferred solvents are alcohols, particularly methanol.

The resolution procedure is usually carried out at room temperature, but may be carried out at a higher or lower temperature. In order to obtain a uniform solution, the mixture may be heated up to the boiling point of the solvent, and the reaction mixture may optionally be cooled gradually in order to obtain a pure diastereomer salt.

By the resolution procedure, the diasteromer salt having less solubility is crystallized out from the reaction mixture. In case of using S-2-amino-1,1-diphenylpropanol or S-2-amino-3-methyl-1,1,-diphenylbutanol as the resolving reagent, the diastereomer salt having less solubility is a salt of L-threo-2-(3,4-dibenzyloxyphenyl)-N-carbobenzyloxyserine, and a salt of D-threo-3-(3,4-dibenzyloxyphenyl)-N-carbobenzyloxyserine remains in the solution. In case of using S-2-amino-4-methyl-1,1-diphenylpentanol as the resolving reagent, the diastereomer salt having less solubility is a salt of D-threo-3-(3,4-dibenzyloxyphenyl)-N-carobenzyloxyserine, and a salt of L-threo-3-(3,4-dibenzyloxyphenyl)-N-carbobenzyloxyserine remains in the solution.

The diastereomer salt crystallized out from the reaction mixture is recrystallized from an alcohol or ketone solvent in order to improve the optical purity thereof. The diastereomer salt remaining in the mixture can be isolated from the mixture by concentrating the filtrate obtained after removing the diastereomer salt which first crystallized out and then collecting the resulting precipitates.

The diastereomer salts thus resolved can each be decomposed into the optically active (D- or L-) threo-3-(3,4-dibenzyloxyphenyl)-N-carbobenzyloxyserine [I] by conventional methods. For example, the diastereomer salt which first crystallizes out or which is obtained from the filtrate is added to an aqueous solution of a mineral acid, such as hydrochloric acid, sulfuric acid, phosphoric acid, or the like, and thereby the desired optically active (D- or L-) threo-3-(3,4-dibenzyloxyphenyl)-N-carbobenzyloxyserine [I] is obtained from the organic layer. The resolving reagent, that is, the optically active amino alcohol derivative [II] moves into the aqueous layer.

The optically active (D- or L-) threo-3-(3,4-dibenzyloxyphenyl)-N-carbobenzyloxyserine thus obtained is then subjected to hydrogenolysis to produce the corresponding optically active (D- or L-) threo-DOPS. The hydrogenolysis can be carried out by treating the resolved salt with hydrogen in an appropriate solvent in the presence of a catalyst at a temperature of 0° to 100° C. under atmospheric or higher pressure. Suitable examples of the catalyst are palladium, platinum, nickel, or the like, which may be carried on an appropriate carrier such as active carbon, barium carbonate, or the like. Suitable examples of the solvent are lower alcohols having 1 to 4 carbon atoms such as methanol, ethanol, or the like, or an aqueous mixture of the alcohols.

In order to promote the hydrogenolysis or to improve the solubility of the reaction product, an appropriate acid may be added to the reaction mixture in an amount of 0.8 to 2.0 moles to 1 mole of the resolved salt. Suitable examples of the acid are mineral acids such as hydrochloric acid, sulfuric acid, or the like or organic acids such as acetic acid, methanesulfonic acid, or the like.

After the hydrogenolysis is completed, the reaction mixture is filtered to remove the catalyst, and concentrated, and when an acid is added, it is neutralized, and thereby, the desired optically active (D- or L-) threo-DOPS can be obtained in the crystalline form.

The starting racemic threo-3-(3,4-dibenzyloxyphenyl)-N-carbobenzyloxyserine [I] is a known compound and can easily be obtained by introducing a carbobenzyloxy group onto the amino group of racemic threo-3-(3,4-dibenzyloxyphenyl)serine which can advantageously be produced by a process found by the present inventors (cf. Japanese Patent Publication (unexamined) No. 19931/1979). The optically active amino alcohol derivatives [II] used as the resolving reagent are also known [cf. J. Chem. Soc., 287 (1925), 785 (1926; J. Pharm. Soc., Japan 48, 46 (1928)] and can easily be produced from an optically active α-amino acid by a single step as shown in the following reaction scheme A:

Reaction Scheme A

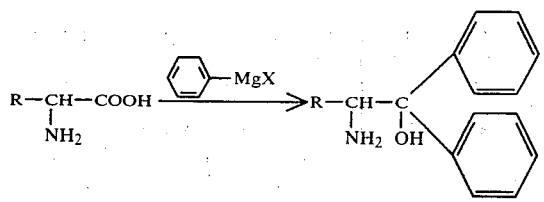

wherein R is as defined above, and X is a halogen atom.

The present invention is illustrated by the following Examples, but is not limited thereto.

EXAMPLE 1

Racemic threo-3-(3,4-dibenzyloxyphenyl)-N-carbobenzyloxyserine (65 g) is dissolved in methanol (650 g) at 50° C., and therein is dissolved S-2-amino-1,1-diphenylpropanol (28.0 g). The mixture is cooled to 30° C. over a period of one hour. The mixture is again heated to 50° C. and is then cooled to 25° C. over a period of 2 hours and is agitated under ice-cooling for 3 hours. The precipitated crystals are collected to obtain L-threo-3-(3,4-dibenzyloxyphenyl)-N-carbobenzyloxyserine.S-2-amino-1,1-diphenylpropanol salt (40.5 g). Melting point 151°–153° C., $[\alpha]_D^{20}$ −30.5° (c=1, tetrahydrofuran)

The salt (20 g) thus obtained is decomposed by treating with 3% hydrochloric acid to give L-threo-3-(3,4-dibenzyloxyphenyl)-N-carbobenzyloxyserine in the crystalline form (13.5 g). Melting point 130-°–132° C., $[\alpha]_D^{20}$ −18.3° (c=1, methanol)

The filtrate obtained after removing the diastereomer salt is concentrated and is decomposed with 3% hydrochloric acid to give D-threo-3-(3,4-dibenzyloxyphenyl)-N-carbobenzyloxyserine in the crystalline form (34 g). Melting point 128°–132° C., $[\alpha]_D^{20}$ +16.5° (c=1, methanol)

EXAMPLE 2

Racemic threo-3-(3,4-dibenzyloxyphenyl)-N-carbobenzyloxyserine (2.0 g) is dissolved in 20% aqueous methanol (20 ml), and therein is dissolved with agitation S-2-amino-1,1-diphenylpropanol (0.86 g) at 55° C. The mixture is cooled to 30° C. over a period of 3 hours. After the reaction mixture is allowed to stand overnight, the precipitated crystals are collected by filtration to give L-threo-3-(3,4-dibenzyloxyphenyl)-N-carbobenzyloxyserine.-2-amino-1,1-diphenylpropanol salt (1.52 g). Melting point 150°–153° C.

The salt thus obtained is decomposed with 3% hydrochloric acid and extracted with ethyl acetate to give L-threo-3-(3,4-dibenzyloxyphenyl)-N-carbobenzyoxyserine (0.95 g). Melting point 118°–122° C., $[\alpha]_D^{20}$ −16.3° (c=1, methanol)

EXAMPLE 3

Racemic threo-3-(3,4-dibenzyloxyphenyl)-N-carbobenzyloxyserine (0.8 g) and R-2-amino-1,1-diphenylpropanol (0.8 g) are dissolved in ethyl acetate (10 ml). The mixture is allowed to stand for 5 days, and thereby there is obtained D-threo-3-(3,4-dibenzyloxyphenyl)-N-crbobenzyloxyserine.R-2-amino-1,1-diphenylpropanol salt (0.45 g). Melting point ⅛°–152° C.

The salt thus obtained is decomposed with 3% hydrochloric acid and extracted with ethyl acetate to give D-threo-3-(3,4-dibenzyloxyphenyl)-N-carbobenzyloxyserine (0.26 g). Melting point 148°–152° C., $[\alpha]_D^{20}$ −15.0° (c=1, methanol)

EXAMPLE 4

Racemic threo-3-(3,4-dibenzyloxyphenyl)-N-carbobenzyloxyserine (0.53 g) and S-2-amino-3-methyl-1,1-diphenylbutanol (0.26 g) are dissolved in methanol (3 ml). After the mixture is allowed to stand at 5° C. overnight, the precipitated crystals are collected by filtration to give L-threo-3-(3,4-dibenzyloxyphenyl)-N-carbobenzyloxyserine.S-2-amino-3-methyl-1,1-diphenylbutanol salt (0.35 g). Melting point 125°–130° C.

The salt thus obtained is decomposed with 3% hydrochloric acid and extracted with ethyl acetate to give L-threo-3-(3,4-dibenzyloxyphenyl)-N-carbobenzyloxyserine (0.20 g). $[\alpha]_D^{20}$ −6.0° (c=1, methanol)

EXAMPLE 5

Racemic threo-3-(3,4-dibenzyloxyphenyl)-N-carbobenzyloxyserine (2.1 g) and S-2-amino-4-methyl-1,1-diphenylpentanol (1.1 g) are dissolved in methanol (15 ml). The mixture is allowed to stand overnight, and the precipitated crystals are collected by filtration to give D-threo-3-(3,4-dibenzyloxyphenyl)-N-carbobenzyloxyserine.S-2-amino-4-methyl-1,1-diphenylpentanol salt (1.35 g). Melting point 106°–110° C.

The salt thus obtained is decomposed with 3% hydrochloric acid and extracted with ethyl acetate to give D-threo-3-(3,4-dibenzyloxyphenyl)-N-carbobenzyloxyserine (0.84 g). Melting point 90°–96° C., $[\alpha]_D^{20}$ +14.0° (c=1, methanol)

EXAMPLE 6

L-Threo-3-(3,4-dibenzyloxyphenyl)-N-carbobenzyloxyserine, $[\alpha]_D^{20}$ −19.3° (c=1, methanol) (20 g) is dissolved in a mixture of methanol (300 g) and water (10 g). To the solution are added concentrated hydrochloric acid (4.9 g) and 5% palladium-active carbon (0.6 g), and the mixture is subjected to hydrogenolysis with hydrogen gas at room temperature under atmospheric pressure. After absorption of hydrogen gas is no longer observed, the reaction mixture is filtered to remove undissolved materials, and the mixture is neutralized with a 5 N aqueous sodium hydroxide solution. The mixture is agitated under ice-cooling for 2 hours. The precipitated crystals are collected by filtration to give L-threo-3-(3,4-dihydroxyphenyl)serine (8.0 g). Melting point 203°–206° C. (decomp.)

The compound thus obtained is recrystallized from water (450 g) containing L-ascorbic acid (80 mg) to give a purified product (5.7 g). Melting point 229°–232° C. (decomp.), $[\alpha]_D^{20}$ −42.0° (c=1, 1 N hydrochloric acid)

EXAMPLE 7

D-Threo-3-(3,4-dibenzyloxyphenyl)-N-carbobenzyloxyserine, $[\alpha]_D^{20}$ +19.1° (c=1.2, methanol) (20.3 g) is dissolved in a mixture of methanol (370 ml) and 1 N hydrochloric acid (43 ml). To the mixture is added 5% palladium-active carbon (1.7 g), and the mixture is subjected to hydrogenolysis in the same manner as in Example 6. After absorption of hydrogen gas is no longer observed, the undissolved materials are removed by filtration, and then the filtrate is neutralized with diethylamine. The mixture is agitated under ice-cooling for 2 hours. The precipitated crystals are collected by filtration to give D-threo-3-(3,4-dihydroxyphenyl)serine (8.3 g). This compound is recrystallized from water (500 ml) containing L-ascorbic acid (80 mg) to give a purified product (6.3 g). Melting point 213°–219° C., $[\alpha]_D^{20}$ +41.2° (c=1.1, 1 N hydrochloric acid).

What is claimed is:

1. A process for the production of optically active (D- or L-) threo-3-(3,4-dihydroxyphenyl)serine, which comprises subjecting racemic threo-3-(3,4-dibenzyloxyphenyl)-N-carbobenzyloxyserine of the formula:

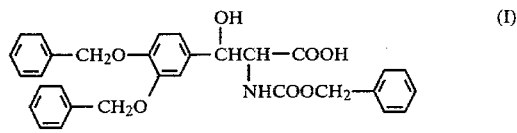

to optical resolution by using as a resolving reagent an equimolar or less amount sufficient to provide optical resolution of an optically active amino acid alcohol derivative of the formula:

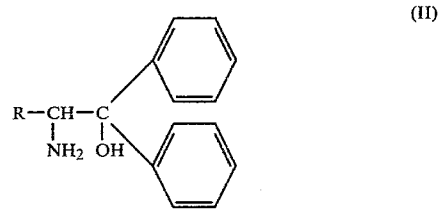

wherein R is methyl, isopropyl or isobutyl, in a solvent medium, separating the insoluble diastereomer salt, producing the optically active free acid therefrom by treatment with an aqueous mineral acid, and then subjecting the resulting optically active (D- or L-) threo-3-(3,4-dibenzyloxyphenyl)-N-carbobenzyloxyserine to hydrogenolysis.

2. The process according to claim 1, wherein the resolving reagent is a compound of the formula (II) wherein R is methyl.

3. The process according to claim 1, wherein the resolving reagent is a compound of the formula (II) wherein R is isopropyl.

4. The process according to claim 1, wherein the resolving reagent is a compound of the formula (II) wherein R is isobutyl.

5. The process according to claim 1, wherein the resolving reagent (II) is used in an amount of 0.5 to 1 mole per 1 mole of the starting compound (I).

6. The process according to claim 1, wherein the optical resolution is carried out in a solvent selected from an alcohol having 1 to 4 carbon atoms and an aqueous mixture thereof.

7. The process according to claim 6, wherein the alcohol is methanol.

* * * * *

UNITED STATES PATENT AND TRADEMARK OFFICE
CERTIFICATE OF CORRECTION

PATENT NO. : 4,319,040
DATED : March 9, 1982
INVENTOR(S) : Ohashi et al

It is certified that error appears in the above—identified patent and that said Letters Patent is hereby corrected as shown below:

In the category "[75] Inventors", change

"Kikuo Ioshizumi" to --Kikuo Ishizumi--

Signed and Sealed this

Fourth Day of May 1982

[SEAL]

Attest:

GERALD J. MOSSINGHOFF

Attesting Officer     Commissioner of Patents and Trademarks